United States Patent [19]
Light et al.

[11] Patent Number: 5,952,470
[45] Date of Patent: Sep. 14, 1999

[54] METHOD FOR SEPARATING UNMODIFIED HEMOGLOBIN FROM CROSS-LINKED HEMOGLOBIN

[75] Inventors: William R. Light, Natick; Maria S. Gawryl, Charlestown; Anthony J. Laccetti, North Andover; Robert A. Houtchens, Milford, all of Mass.

[73] Assignee: Biopure Corporation, Cambridge, Mass.

[21] Appl. No.: 08/477,916

[22] Filed: Jun. 7, 1995

[51] Int. Cl.$^6$ .............................. C07K 1/30; C07K 14/805
[52] U.S. Cl. ..................... 530/385; 530/412; 530/419; 514/6
[58] Field of Search .................... 514/6; 530/385, 530/412, 419

[56] References Cited

U.S. PATENT DOCUMENTS

| | | | |
|---|---|---|---|
| Re. 32,089 | 3/1986 | Blatt et al. | 210/651 |
| Re. 34,271 | 6/1993 | Walder | 530/385 |
| 3,858,014 | 12/1974 | Watanabe et al. | 424/366 |
| 4,001,200 | 1/1977 | Bonsen et al. | 260/112.5 R |
| 4,001,401 | 1/1977 | Bonsen et al. | 424/177 |
| 4,053,590 | 10/1977 | Bonsen et al. | 424/177 |
| 4,061,736 | 12/1977 | Morris et al. | 424/177 |
| 4,136,093 | 1/1979 | Bonhard et al. | 260/112.5 R |
| 4,598,064 | 7/1986 | Walder | 514/6 |
| 4,826,811 | 5/1989 | Sehgal et al. | 514/6 |
| 4,857,636 | 8/1989 | Hsia | 530/385 |
| 5,084,558 | 1/1992 | Rausch et al. | 530/385 |
| 5,189,146 | 2/1993 | Hsia | 530/385 |
| 5,194,590 | 3/1993 | Sehgal et al. | 530/385 |
| 5,296,465 | 3/1994 | Rausch et al. | 514/6 |
| 5,464,814 | 11/1995 | Sehgal | 514/6 |
| 5,532,352 | 7/1996 | Pliura et al. | 540/145 |

*Primary Examiner*—Cecilia J. Tsang
*Assistant Examiner*—Anish Gupta
*Attorney, Agent, or Firm*—Hamilton, Brook, Smith & Reynolds, P.C.

[57] ABSTRACT

A method for separating unmodified hemoglobin from cross-linked hemoglobin in a hemoglobin solution. The method involves contacting the hemoglobin solution with a least one dissociating agent to form a dissociation solution wherein unmodified tetrameric hemoglobin is dissociated to form hemoglobin dimers. The hemoglobin dimers are then separated from the dissociation solution, while retaining the cross-linked hemoglobin in the dissociation solution.

20 Claims, 1 Drawing Sheet

METHOD FOR SEPARATING UNMODIFIED HEMOGLOBIN FROM CROSS-LINKED HEMOGLOBIN

BACKGROUND OF THE INVENTION

There exists a need for a blood-substitute to treat or prevent hypoxia resulting from blood loss (e.g, from acute hemorrhage or during surgical operations), resulting from anemia (e.g., pernicious anemia or sickle cell anemia), or resulting from shock (e.g, volume deficiency shock, anaphylactic shock, septic shock or allergic shock).

The use of blood and blood fractions as in these capacities as a blood-substitute is fraught with disadvantages. For example, the use of whole blood often is accompanied by the risk of transmission of hepatitis-producing viruses and AIDS-producing viruses which can complicate patient recovery or result in patient fatalities. Additionally, the use of whole blood requires blood-typing and cross-matching to avoid immunohematological problems and interdonor incompatibility.

Hemoglobin, as a blood-substitute, possesses osmotic activity and the ability to transport and transfer oxygen. However, aqueous hemoglobin exists in equilibrium between the tetrameric (MW 68,000) and dimeric (MW 34,000) forms. Hemoglobin dimers are excreted by the kidney and result in rapid intravascular elimination of hemoglobin solutions with such solutions typically having a 2–4 hour plasma half-life.

Efforts have been directed to overcome the inherent limitations of hemoglobin solutions by molecularly modifying the hemoglobin. Intramolecularly and intermolecularly cross-linking of hemoglobin has generally reduced renal elimination and increased intravascular retention time.

However, solutions of cross-linked hemoglobin still typically contain a significant fraction of unmodified tetrameric hemoglobin. This unmodified tetrameric hemoglobin can convert to dimeric hemoglobin and then be excreted from the body, thereby reducing the average intravascular retention time for cross-linked hemoglobin blood-substitutes. Furthermore, current means for separation, such as standard filtration, do not adequately distinguish between unmodified tetrameric hemoglobin and modified tetrameric hemoglobin.

Thus, in spite of the recent advances in the preparation of cross-linked hemoglobin blood-substitutes, the need continues to exist for a method to effectively separate unmodified hemoglobin from a solution of an intramolecularly and/or intermolecularly cross-linked hemoglobin blood-substitute to improve the average intravascular retention time of the blood-substitute and to prevent significant levels of renal excretion of hemoglobin.

SUMMARY OF THE INVENTION

The present invention relates to a method for separating unmodified hemoglobin from cross-linked hemoglobin in a hemoglobin solution. The method involves contacting the hemoglobin solution with a least one dissociating agent to form a dissociation solution wherein unmodified tetrameric hemoglobin is dissociated to form hemoglobin dimers. The hemoglobin dimers are then separated from the dissociation solution, while retaining the cross-linked hemoglobin in the dissociation solution.

The advantages of this invention include providing a blood-substitute with an improved intravascular retention time, a reduction or elimination of significant renal elimination of hemoglobin and the side effects associated therewith, a suitable oncotic pressure, and reduced hypertensive effects.

DETAILED DESCRIPTION OF THE INVENTION

Figure 1:
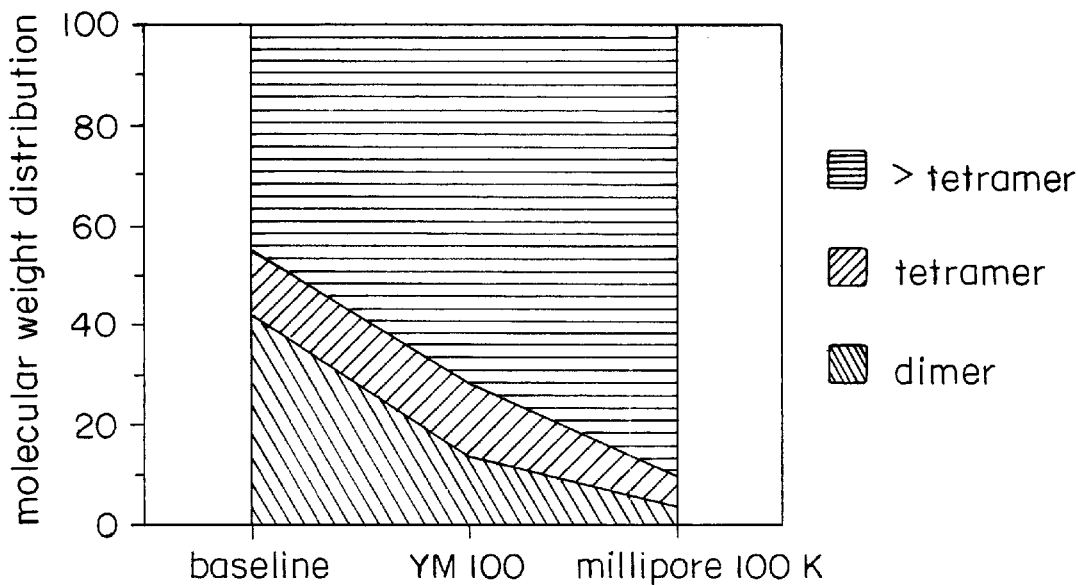
FIG. 1 represents a schematic flow diagram of a method for separating unmodified hemoglobin from modified hemoglobin blood-substitute according to the present invention.
Figure 2:
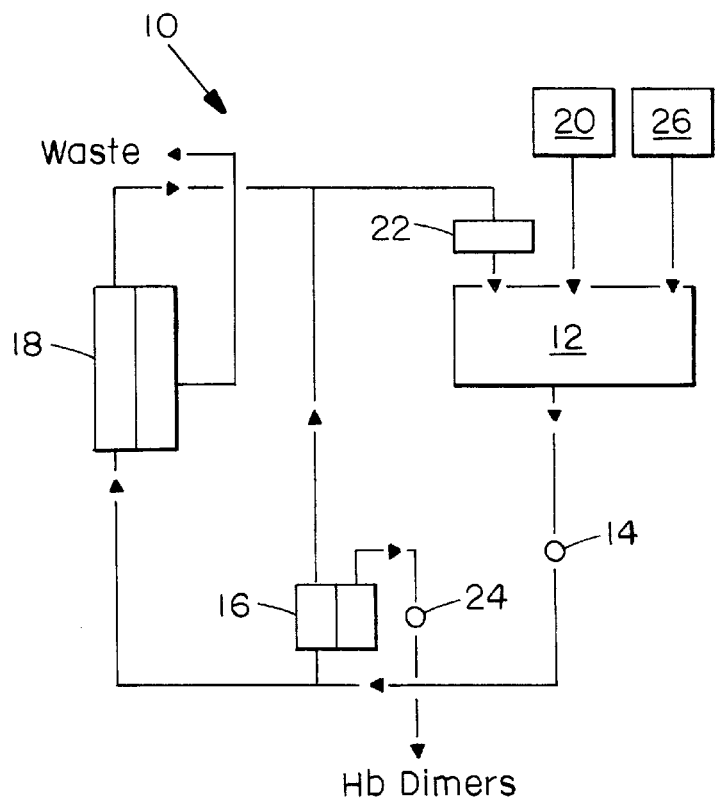
FIG. 2 represents the molecular weight distribution of a modified hemoglobin polymer, in solution, treated according to the method of this invention.

Hemoglobin (Hb) suitable for Hb solutions of this invention can be derived from new, old or outdated blood from humans and other vertebrates, such as cattle, pigs, sheep and chickens. In addition, transgenically-produced hemoglobin, such as the transgenically-produced Hb described in *BIO/TECHNOLOGY*, 12: 55–59 (1994), and recombinantly produced hemoglobin, such as the recombinantly produced hemoglobin described in *Nature*, 356: 258–260 (1992), are also suitable for Hb solutions of this invention.

The blood can be collected from live or freshly slaughtered donors. Examples of suitable methods for obtaining hemoglobin, derived from red blood cells, are described in U.S. Pat. Nos. 5,084,558 and 5,296,465, issued to Rausch et al. The teachings of U.S. Pat. Nos. 5,084,558 and 5,296,465 are incorporated herein by reference in their entirety.

In a preferred embodiment, hemoglobin is derived from red blood cells, or recombinant bacteria, as described in co-pending U.S. patent application Ser. No. 08/484,775, filed Jun. 7, 1995, the teachings of which are incorporated herein by reference in their entirety.

Suitable hemoglobin solutions comprise aqueous solutions of dissolved Hb wherein the dissolved Hb includes unmodified Hb in addition to modified tetrameric Hb and/or polymerized Hb.

Unmodified hemoglobin, as defined herein, is hemoglobin in an non-dissociated tetrameric which can dissociate in aqueous solution into Hb dimers, and dissociated Hb dimers. Hb dimers can further dissociated into Hb subunits (monomers). Unmodified Hb may be free (not polymerized) within a Hb solution and/or may be intermolecularly cross-linked into a polymer chain within the Hb solution.

Cross-linked hemoglobin, as defined herein, is which is modified and/or polymerized. For unmodified Hb contained in a Hb polymer chain, any dimers which are not intermolecularly cross-linked can be dissociated and separated by the method of invention.

Modified hemoglobin, as defined herein, is Hb which has been intramolecularly cross-linked to preclude significant dissociation, in aqueous solution, of Hb tetramers into Hb dimers.

In polymerized hemoglobin, Hb tetramers are intermolecularly cross-linked to form a Hb polymer chain. A hemoglobin polymer can contain modified hemoglobin, unmodified hemoglobin, or a combination thereof. In this method, Hb dimers can be dissociated from unmodified Hb tetramers within a polymer chain, in aqueous solution, if the Hb dimer is not intermolecularly bound to other Hb tetramers.

In the method of the present invention, at least one dissociation agent is contacted with hemoglobin in an aqueous solution to form a dissociation solution. Suitable dissociation agents are water-soluble agents at a concentration within an aqueous solution which, when exposed to unmodified hemoglobin tetramers, result in breaking at least a portion of the hydrogen bonds between Hb dimers in the unmodified Hb tetramers to dissociate the unmodified Hb tetramers into independent $\alpha_1\beta_1$ and/or $\alpha_2\beta_2$ Hb dimers. The Hb dimers may also further dissociate to form Hb subunits ($\alpha_1$, $\alpha_2$, $\beta_1$ and $\beta_2$).

A dissociation solution typically contains a concentration of dissolved dissociation agent having a normality of about 1 gm-equivalent of dissociation agent per liter of dissociation solution, or more. Preferably, a the concentration of dissociation agent within a dissociation solution is greater than about 1.4 N.

Dissociation agents must be ionic or strongly polar when in an aqueous solution. Examples of suitable dissociation agents include, water soluble inorganic salts (e.g., salts of sodium, calcium, magnesium and zinc), water soluble organic salts (e.g., triethylamine chloride), and water soluble organic amines (e.g., guanidine). Preferably, a dissociation agent is an inorganic salt, or salts, containing at least one multivalent metal cation such as $Ca^{+2}$, $Mg^{+2}$ or $Zn^{+2}$.

Water soluble, as defined herein, means that the material is sufficiently soluble in water at room temperature to form a solution with a concentration sufficient, when contacted with Hb, to result in breaking at least a portion of the hydrogen bonds between Hb dimers in unmodified Hb tetramers.

The dissociation agent can be dissolved in an aqueous solution prior to being contacted with the Hb solution or conversely, the dissociation agent can be a solid, in powder or particulate form, when contacted with an aqueous Hb solution wherein the dissociation agent will then dissolve.

Either the dissociation agent or the Hb solution can be added to the other, or they can be added together. The dissociation agent and the Hb solution can be contacted by batch feed or continuous feed.

In a preferred embodiment, the dissociation agent is mixed with the Hb solution by a suitable mixing means. More preferably, the mixing means in a low shear mixing device as described in co-pending U.S. patent application Ser. No. 08/484,775, filed Jun. 7, 1995, the teachings of which are incorporated herein by reference in their entirety.

Examples of suitable hemoglobin solutions include hemoglobin solutions which have a stabilized 2,3-diphosphoglycerate level, as described in U.S. Pat. No. 3,864,478, issued to Bonhard; cross-linked hemoglobin, as described in U.S. Pat. No. 3,925,344, issued to Mazur, or in U.S. Pat. Nos. 4,001,200, 4,001,401 and 4,053,590, issued to Bonsen et al., or in U.S. Pat. No. 4,061,736, issued to Morris et al., or in U.S. Pat. No. 4,473,496, issued to Scannon; stroma-free hemoglobin, as described in U.S. Pat. No. 3,991,181, issued to Doczi, or in U.S. Pat. No. 4,401,652, issued to Simmonds et al. or in U.S. Pat. No. 4,526,715, issued to Kothe et al.; hemoglobin coupled with a polysaccharide, as described in U.S. Pat. No. 4,064,118, issued to Wong; hemoglobin condensed with pyridoxal phosphate, as described in U.S. Pat. No. 4,136,093, issued to Bonhard et al.; dialdehyde-coupled hemoglobin, as described in U.S. Pat. No. 4,336,248, issued to Bonhard et al.; hemoglobin covalently bound with inulin, as described in U.S. Pat. No. 4,377,512, issued to Ajisaka et al.; hemoglobin or a hemoglobin derivative which is coupled with a polyalkylene glycol or a polyalkylene oxide, as described in U.S. Pat. No. 4,412,989, issued to Iwashita et al., or U.S. Pat. No. 4,670,417, issued to Iwasaki et al., or U.S. Pat. No. 5,234,903, issued to Nho et al.; pyrogen- and stroma-free hemoglobin solution, as described in U.S. Pat. No. 4,439, 357, issued to Bonhard et al.; stroma-free, non-heme protein-free hemoglobin, as described in U.S. Pat. No. 4,473,494, issued to Tye; modified cross-linked stroma-free hemoglobin, as described in U.S. Pat. No. 4,529,719, issued to Tye; stroma-free, cross-linked hemoglobin, as described in U.S. Pat. No. 4,584,130, issued to Bucci et al.; α-cross-linked hemoglobin, as described in U.S. Pat. No. 4,598,064 and U.S. Pat. No. Re. 34,271, issued to Walder et al.; stable aldehyde polymerized hemoglobin, as described in U.S. Pat. No. 4,857,636, issued to Hsia; hemoglobin covalently linked to sulfated glycosaminoglycans, as described in U.S. Pat. No. 4,920,194, issued to Feller et al.; modified hemoglobin reacted with a high molecular weight polymer having reactive aldehyde constituents, as described in U.S. Pat. No. 4,900,780, issued to Cerny; hemoglobin cross-linked in the presence of sodium tripolyphosphate, as described in U.S. Pat. No. 5,128,452, issued to Hai et al.; stable, polyaldehyde polymerized hemoglobin, as described in U.S. Pat. No. 5,189,146, issued to Hsia; and β-cross-linked hemoglobin, as described in U.S. Pat. No. 5,250,665, issued to Kluger et al. The teachings of the patents and patent applications noted above are hereby incorporated by reference in their entirety.

Other examples of suitable Hb solutions are described, for example, in U.S. Pat. No. 5,296,465, issued to Rausch et al. The teachings of U.S. Pat. No. 5,296,465 are incorporated herein by reference in their entirety.

In a preferred embodiment, hemoglobin used in the method of invention is in the form of a polymerized hemoglobin blood-substitute. Examples of suitable polymerized hemoglobin blood-substitutes are described in U.S. Pat. Nos. 5,084,558 and 5,217,648, issued to Rausch et al., co-pending U.S. patent application Ser. No. 08/484,775, filed Jun. 7, 1995, and, the teachings of which are incorporated herein by reference.

The composition of Hb blood-substitutes preferred for use in the method of invention are sterile aqueous solutions having less than 0.5 endotoxin units/ml, a methemoglobin content that will not result in a significant reduction in oxygen transport/transfer capacity, a total hemoglobin concentration between about 1 to about 25 g Hb/dl, a physiologic pH and a chloride ion concentration of less than 35 meq/l.

The term "endotoxin" refers to the cell-bound lipopolysaccharides produced as a part of the outer layer of bacterial cell walls, which under many conditions are toxic. An endotoxin unit (EU) has been defined, by the United States Pharmacopeial Convention of 1983, page 3013, as the activity contained in 0.1 nanograms of U.S. reference standard lot EC-5. One vial of EC-5 contains 10,000 EU.

Conditions within the dissociation solution, such as pH and temperature, are within ranges which will not significantly reduce the ability of the Hb to transport and release oxygen, such as would occur from denaturing the Hb. Such suitable conditions are as classically known in the art.

The pH of the dissociation solution must be low enough for Hb tetramer dissociation to occur and high enough to preclude significant acid-induced denaturing of the Hb. Typically, pH is maintained between about 4.5 and about 9.5. Preferably, the pH of the dissociation solution is acidic.

In another embodiment, the dissociation solution also contains a buffer to maintain the dissociation solution within a suitable pH range, typically about 4.5 to about 9.5. The buffer can consist of one or more chemical compound.

A preferred buffer comprises 2,2-bis(hydroxy-methyl)-2, 2',2"-nitrilotriethanol (Bis-Tris) with a pH between 5.5 and 8.0.

The dissociation solution can be buffered by adding a solid (powder or particulate) buffer or an aqueous buffer solution to the Hb solution. Further, the buffer can be added to an aqueous solution of the dissociation agent prior to being contacted with the Hb solution.

In yet another embodiment, the dissociation solution further contains a stabilizing agent in an amount suitable to minimize the formation of methemoglobin by auto-oxidation. An example of a suitable amount of a stabilizing agent is a 0.1 mM solution of ethylenediaminetetraacetic acid (EDTA).

Hemoglobin solutions used in this method are typically maintained under conditions sufficient to minimize microbial growth, or bioburden, such as maintaining temperature at less than about 20° C. and above 0° C. Preferably, temperature is maintained at a temperature of about 15° C. or less. More preferably, the temperature is maintained at about 10° C. to about 12° C.

The dissociation solution is then filtered to purify the Hb solution by separating dissociated Hb dimer from modified Hb and/or polymerized Hb. Suitable filters include ultrafilters which will pass in the filtrate components having a molecular weight cutout between about 40,000 Daltons and 100,000 Daltons. During filtration, components of the Hb solution, which are smaller in diameter than modified tetrameric Hb, or which are fluids or dissolved, pass through the filter with the filtrate. However, the modified Hb tetramers and the polymerized Hb generally remains in the retentate.

A 50,000 Dalton ultrafilter is preferred as it will allow separation of Hb dimers from the Hb solution without a significant loss of yield of modified Hb tetramers or polymerized Hb.

In one embodiment, the dissociation solution is only filtered once. Alternately, the dissociation solution can purified by one then one filter in series, wherein the retentate of from a previous filter is further purified by a subsequent filter.

Preferably, the Hb retentate is recirculated continuously through one or more filters, as shown in FIG. 1, thereby continuing to remove dimer as unmodified Hb continues to dissociate in the dissociation solution over time.

In another embodiment, water or an aqueous solution of electrolytes, or preferably of dissociation agent, is added to the dissociation solution before and/or during filtration to at least particularly make up for the fluid volume lost as filtrate during filtration. The water or aqueous solution can be added batchwise or continuously at a rate equal to the rate of filtrate volume loss through the filter.

Water as used in the method of invention may be distilled water, deionized water, water-for-injection (WFI) and/or low pyrogen water (LPW). WFI, which is preferred, is deionized, distilled water that meets U.S. Pharmacological Specifications for water-for-injection. WFI is further described in *Pharmaceutical Engineering*, 11, 15–23 (1991). LPW, which is more preferred, is deionized water containing less than 0.002 EU/ml.

Typically, about 99%, or more, of the unmodified Hb has been separated from the modified Hb and polymeric Hb in the Hb retentate, when the volume of filtrate removed from the Hb solution equals about 500% of the volume of the Hb solution prior to adding the dissociation agent.

When using the Hb solution as a blood-substitute, the hemoglobin in the Hb retentate is then washed and equilibrated by diafiltration with a physiologic buffer to ensure the physiological acceptability of the blood-substitute. Suitable physiologic buffers include buffers that have physiologically acceptable levels of electrolytes (e.g, NaCl, KCl and $CaCl_2$) in WFI. Preferably, the buffer is depyrogenated, such as by filtration with a 10,000 Dalton ultrafilter, and deoxygenated.

A buffer solution can further include a dissolved, non-toxic reducing agent, such as N-acetyl-L-cysteine, cysteine, sodium dithionite or ascorbate, to chemically scavenge oxygen in the blood-substitute to reduce methemoglobin formation. For Hb blood-substitutes, a methemoglobin content of about 25% or more will typically result in a significant reduction in oxygen delivery capacity. It is preferred that methemoglobin content be less than about 15%. In an even more preferred, the methemoglobin content in a Hb blood-substitute be less than or equal to about 10%.

Oxygenation of Hb, similar to dissociation buffers, will also dissociate unmodified hemoglobin into Hb dimers, as shown in Example III. However, oxygenation of Hb also promotes methemoglobin formation.

It is understood that the physiologic buffer and the reducing agent can be added separately, or jointly, to the Hb retentate in a batch or continuous feed mode.

In a preferred embodiment, the Hb retentate is washed by diafilteration against a physiologic buffer until the Hb solution is physiologically acceptable to humans and/or other vertebrates.

Typically, diafiltration continues until the volume of fluid lost through diafiltration across the diafilter is about five times, or more, of the initial volume of the Hb retentate before washing. In a more preferred embodiment diafiltration is continued until about 10 volumes of fluid have been exchanged.

Further description of the use of this method, to remove unmodified Hb from polymeric Hb solutions, is provided in Examples I and II.

In this method, portions of the components for the process for a preparing a stable polymerized hemoglobin blood-substitute are sufficiently sanitized to produce a sterile product. Sterile is as defined in the art, specifically, that the solution meets United States Pharmacopeia requirements for sterility provided in USP XXII, Section 71, pages 1483–1488. Further, portions of components that are exposed to the process stream, are usually fabricated or clad with a material that will not react with or contaminate the process stream. Such materials can include stainless steel and other steel alloys, such as Inconel.

The pump used in this method can be a peristaltic-type, diaphragm-type, gear-type, piston-type or rotary-lobe type pump. Diaphragm-type pumps are available from Branne Lubbem Inc., Buffalo Grove, Ill. Suitable rotary-lobe pumps include the Albin SLP 110 P51 B1 sanitary lobe-rotary pump from Albin Pump Inc., Atlanta, Ga. Rotary-lobe pumps can also be obtained from Waukesha Pumps, Waukesha, Wis.

One embodiment of a system 10, suitable for practicing the method of invention for separating unmodified hemoglobin from a Hb solution contained modified Hb tetramer and/or polymeric Hb, is illustrated in FIG. 1. System 10 includes tank 12, pump 14, purification filter 16 and diafilter 18. Pump 14 takes a suction on tank 12 and recirculates Hb solution through purification filter 16 and/or diafilter 18. It is understood that purification filter 16 and diafilter 18 can be operated in parallel or in series arrangements. Tank 12 contains Hb solution which can be formed within tank 12 or which can be formed prior to being transferred into tank 12.

An amount of an Hb dissociation agent, suitable to dissociate Hb tetrameric molecules into Hb dimers, is then contacted with the Hb solution in system 10 to form a dissociation solution. The dissociation agent is typically introduced into tank 12, from dissociation agent supply 20. However, it is understood that the dissociation agent can be added at other locations in system 10. It is also understood that the dissociation agent can be added to the Hb solution in a batch or continuous feed mode.

The dissociation agent and the Hb solution in the dissociation solution are then mixed by a low shear mixing, specifically static mixer 22. The dissociation agent and the Hb solution are mixed by recirculating the dissociation solution from tank 12, by pump 14 through an orifice, not shown, and static mixer 22.

Static mixer 22 is typically located downstream of pump 14 and upstream of purification filter 16, however, static mixer 22 alternately could be located at other points in system 10.

The unmodified hemoglobin in the dissociation solution then commences to dissociate from unmodified Hb tetramers into Hb dimers. The Hb dimers each have a molecular weight of about 32,000 Daltons.

The dissociation solution is then recirculated through purification filter 16 to remove Hb dimers in the filtrate, and retain modified Hb and polymeric Hb in the Hb retentate. During filtration, components of the dissociation solution, which are smaller in diameter than stabilized tetrameric Hb, or which are fluids, pass through purification filter 16 with the filtrate. Examples of suitable purification filters include ultrafilters with a molecular weight cutout between about 40,000 Daltons and about 100,000 Daltons.

In a continuous feed mode, a liquid or dissolved dissociation agent is added continuously, as makeup, at a rate equal to the rate of filtrate loss through purification filter 16. In another embodiment, the volume of filtrate discharged through purification filter 16 is regulated by filtrate pump 24.

Separation of unmodified Hb from the Hb retentate is typically complete when the volume of filtrate drained from purification filter 16 equals about 500% of the volume of Hb solution contained in tank 22 prior to adding dissociation agent to system 10.

In another embodiment, the Hb retentate is then washed and equilibrated by diafiltration with a physiologic buffer to make the Hb retentate physiologically acceptable as a blood-substitute. A physiologic buffer is introduced into tank 12, from physiologic buffer supply 26. However, it is understood that the physiologic buffer can be added at any location in system 10. It is also understood that the physiologic buffer can be added to the Hb retentate in a batch or continuous feed mode.

A preferred physiologic buffer includes 27 mM sodium lactate, 12 mM N-acetyl-L-cysteine, 115 mM NaCl and 1.36 mM $CaCl_2$ in WFI (pH 8).

The Hb retentate is then diafiltered by recirculating the Hb retentate and physiological buffer from tank 12, by pump 14 through static mixer 22 and diafilter 18. Diafilter 18 is located downstream of static mixer 22 and upstream of tank 12. Diafiltration continues until the blood-substitute is physiologically acceptable. Typically, the blood-substitute is physiologically acceptable when the volume of fluid lost through diafiltration across diafilter 18 is at least five times the initial volume of the Hb retentate in system 10.

During Hb dissociation and Hb retentate diafiltration, the Hb temperature is maintained at approximately 8° C. to 12° C. in tank 14. An example of an acceptable means for controlling the Hb temperature is by cooling the outside of tank 14 through use of an ethylene glycol jacketed cooling system, not shown.

The invention will be further illustrated by the following non-limiting examples.

EXAMPLE I

Diafiltration of Deoxygenated Hb Solution Containing a Higher Concentration Dissociation Buffer A polymerized Hb solution was formed according to the method described in Example 1 of U.S. Pat. No. 5,084,558, issued to Rausch et al. This Hb solution was analyzed by gel permeation chromatography (GPC) and found to comprise about 45% Hb dimers, about 15% unmodified Hb tetramers, and about 40% polymerized Hb molecules which were larger than unmodified tetramers.

One liter of a dissociation buffer containing 1.5 M $MgCl_2$, 0.1 M Bis-Tris and 0.2 mM EDTA (pH 6.5) was added to one liter of the Hb solution. This mixture was then recirculated through a 100 kD polysulfone ultrafilter (Millipore Catalog No. PTHK 000C5) to concentrate the mixture to a volume of one liter. The concentrated mixture was subsequently diafiltered with 11 volumes of a dissociation buffer comprising 0.7 M $MgCl_2$, 0.05 M Bis-Tris and 0.1 mM EDTA (pH 6.5). The filtered Hb solution was then washed and equilibrated with a deoxygenated buffer containing 27 mM sodium lactate, 12 mM N-acetyl cysteine, 115 mM NaCl, 4 mM KCl, and 1.36 mM $CaCl_2$ in WFI. The molecular weight distribution of the resulting Hb solution was then analyzed by GPC.

The results of these analyses are shown in FIG. II. The Hb solution was then found to have a final composition of about 5% Hb dimers, about 10% Hb tetramers and about 85% polymerized Hb molecules which were larger than tetramers.

EXAMPLE II

Diafiltration of Deoxyqenated Hb Solution Containing a Lower Concentration Dissociation Buffer One hundred seventy mLs of a dissociation buffer containing 0.75 M $MgCl_2$, 0.05 M Bis-Tris and 0.1 mM EDTA (pH 7.5) was added to 15 mLs of the initial polymerized Hb solution of Example I and then 15 mLs of a two-fold concentrate of the dissociation buffer was added. The Hb solution was then recirculated through a Chemineer, Inc./Kenics static mixer and then diafiltered by a 100 kD ultrafilter (Amicon YM 100, Catalog No. 14451) to obtain 200 mls of Hb solution.

The Hb solution was then diafiltered with 3 volume exchanges of the dissociation buffer and lastly washed and equilibrated with a deoxygenated buffer containing 27 mM sodium lactate, 12 mM N-acetyl cysteine, 115 mM NaCl, 4 mM KCl, and 1.36 mM $CaCl_2$ in WFI. The molecular weight distribution of the resulting Hb solution was then analyzed by GPC.

The results of these analyses are shown in FIG. II. The Hb solution was then found to have a final composition of about 15% Hb dimers, about 15% Hb tetramers and about 70% polymerized Hb molecules which were larger than tetramers. Thus, the method of invention was effective in reducing the content of unmodified hemoglobin in the polymerized Hb solutions.

EXAMPLE III

Diafiltration of Oxygenated and Deoxygenated Hb Solutions Without a Dissociation Buffer A polymerized Hb solution was formed according to the method described in Example 1 of copending U.S. patent application Ser. No. 08/484,775, filed on Jun. 7, 1995. This Hb solution was analyzed by GPC and found to comprise about 3.5% Hb dimers, 31% unmodified Hb tetramers and about 65.5% polymerized Hb molecules which were larger than unmodified tetramers.

Two liters of the Hb solution were oxygenated through an oxygenation cartridge with a gaseous mixture, comprising 98% oxygen and 2% carbon dioxide, until 95% oxygenated Hb valves were obtained by a co-oximeter (Co-Oximeter Model #482; Instrumentation Laboratory, Lexington, Mass.).

The oxygenated Hb solution was then diafiltered with 7 volumes of an oxygenated buffer solution containing 27 mM solution lactate, 12 mM N-acetyl-L-cysteine, 115 mM NaCl, 4 mM KCl and 1.4 mM $CaCl_2$ in WFI against a 100 kD ultrafilter. Throughout this process, the Hb solution was not contacted with any dissociation buffer.

The molecular weight distribution of the resulting Hb solution was then analyzed by GPC. The molecular weight distribution was found to be 0.5% dimer and 2.7% unmodified tetramer and about 96.8% polymerized Hb molecules which were larger than unmodified tetramers.

This entire procedure was then repeated on another sample of the same polymerized Hb solution, with the exception that the Hb solution was not oxygenated prior to diafiltration. The molecular weight distribution of the resulting Hb solution was found by GPC to be 2.2% dimer, 2.5% unmodified tetramer and about 95.3% polymerized Hb molecules which were larger than unmodified tetramers.

The results of these procedures show that oxygenation of hemoglobin likewise promotes the dissociation of unmodified Hb tetramer to Hb dimers. However, oxygenation also promotes the formation of the undesirable methemoglobin.

EXAMPLE IV

Molecular Weight Analysis

Molecular weight was determined by conducting gel permeation chromatography (GPC) on the hemoglobin solutions under dissociating conditions. This method of analysis results in the separation of hemoglobin polymers on the basis of size, with larger molecules eluting faster than smaller molecules. By comparison to protein molecular weight standards, it is possible for correlate elution time with the molecular weights of the hemoglobin products.

In this analysis, a representative sample of the hemoglobin product was analyzed for molecular weight distribution. The hemoglobin product was diluted to 4 mg/mL within a mobile phase of 50 mM Bis-Tris (pH 6.5), 750 mM $MgCl_2$, and 0.1 mM EDTA. The diluted sample was injected onto a HPLC TosoHaas G3000SW column. Flow rate is 0.5 ml/min. and ultraviolet detection was set at @280 nm.

Equivalents

Those skilled in the art will recognize, or be able to ascertain using no more than routine experimentation, many equivalents to the specific embodiments of the invention described herein. These and all other such equivalents are intended to be encompassed by the following claims.

We claim:

1. A method for dissociating and separating unmodified hemoglobin dimers from intermolecularly cross-linked hemoglobin, comprising the steps of:
    a) contacting a hemoglobin solution of intermolecularly cross-linked hemoglobin with at least one dissociation agent to form a dissociation solution wherein unmodified intermolecularly cross-linked tetrameric hemoglobin is dissociated to form hemoglobin dimers, at least a portion of which are not intermolecularly cross-linked; and
    b) separating said portion of dissociated hemoglobin dimers from the dissociation solution, while retaining intermolecularly cross-linked hemoglobin in said dissociation solution.

2. A method of claim 1 wherein the hemoglobin dimers are separated from the intermolecularly cross-linked hemoglobin by diafiltration.

3. A method of claim 1 wherein the dissociation agent is a water soluble inorganic salt.

4. A method of claim 3 wherein the inorganic salt is a sodium salt.

5. A method of claim 3 wherein the inorganic salt includes a multivalent cation.

6. A method of claim 5 wherein the multivalent cation is selected from the group consisting of $Ca^{+2}$, $Mg^{+2}$ $Zn^{+2}$ and combinations thereof.

7. A method of claim 1 wherein the dissociation agent is a water soluble organic salt.

8. A method of claim 7 wherein the organic salt is a salt of an amine.

9. A method of claim 1 wherein the dissociation agent is a water soluble organic amine.

10. A method of claim 9 wherein the amine is guanidine.

11. A method of claim 1 further comprising the step of mixing the dissociation agent and the hemoglobin solution under low shear conditions.

12. A method of claim 1 further comprising the step of contacting the hemoglobin solution with a buffer.

13. A method of claim 12 wherein the Hb solution is buffered with 2,2-bis(hydroxy-methyl)-2,2',2"-nitrilotriethanol.

14. A method of claim 1 further comprising the step of contacting the Hb solution with a stabilizing agent.

15. A method of claim 14 wherein the stabilizing agent is ethylenediaminetetraacetic acid.

16. A method of claim 1 wherein the unmodified hemoglobin is separated from the dissociation solution by filtering the dissociation solution.

17. A method of claim 1 further comprising the step of washing the cross-linked hemoglobin with a physiologically acceptable buffer, after separating the unmodified hemoglobin from the dissociation solution, to produce a physiologically acceptable hemoglobin blood-substitute.

18. A method for dissociating and filtering unmodified hemoglobin dimers from intermolecularly cross-linked hemoglobin to produce a physiologically acceptable blood-substitute, comprising the steps of:

a) contacting a hemoglobin solution of intermolecularly cross-linked hemoglobin with at least one dissociation agent to form a dissociation solution wherein unmodified intermolecularly cross-linked hemoglobin is dissociated to form hemoglobin dimers, at least a portion of which are not intermolecularly cross-linked;

b) filtering said portion of dissociated hemoglobin dimers from the dissociation solution while retaining intermolecularly cross-linked hemoglobin in said dissociation solution; and c) washing the intermolecularly cross-linked hemoglobin with a physiologic buffer to produce a physiologically acceptable blood substitute.

19. A method of claim 12 wherein the buffer contains sodium lactate and N-acetyl-L-cysteine.

20. A method for dissociating, filtering and washing unmodified hemoglobin dimers from intermolecularly cross-linked hemoglobin, comprising the steps of:

a) mixing a hemoglobin solution of intermolecularly cross-linked hemoglobin with a dissociation agent, a buffer and a stabilizing agent to form a dissociation solution, wherein unmodified intermolecularly cross-linked hemoglobin dissociates to form hemoglobin dimers, at least a portion of which are not intermolecularly cross-linked, within the dissociation solution;

b) filtering the dissociation solution to separate said portion of dissociated hemoglobin dimers from the intermolecularly cross-linked hemoglobin; and c) washing the dissociation solution with a deoxygenated solution containing sodium lactate, N-acetyl-L-cysteine and physiologic electrolytes.

* * * * *

UNITED STATES PATENT AND TRADEMARK OFFICE
CERTIFICATE OF CORRECTION

PATENT NO.       : 5,952,470
APPLICATION NO.  : 08/477916
DATED            : September 14, 1999
INVENTOR(S)      : William R. Light et al.

Page 1 of 1

It is certified that error appears in the above-identified patent and that said Letters Patent is hereby corrected as shown below:

In Column 12, line 1: Delete "A method of Claim 12" and insert therefor --A method of Claim 18--.

Signed and Sealed this

Twenty-fifth Day of March, 2008

JON W. DUDAS
*Director of the United States Patent and Trademark Office*